(12) United States Patent
Vogel et al.

(10) Patent No.: US 8,388,616 B2
(45) Date of Patent: Mar. 5, 2013

(54) COMPRESSION SLEEVE

(75) Inventors: Bernd Vogel, Karlsruhe (DE); Harald Fischer, Weingarten (DE); Marco Klein, Zwickau (DE)

(73) Assignee: Endosmart Gesellschaft Für Medizintechnik MbH, Stutensee (DE)

( * ) Notice: Subject to any disclaimer, the term of this patent is extended or adjusted under 35 U.S.C. 154(b) by 1873 days.

(21) Appl. No.: 11/363,426

(22) Filed: Feb. 27, 2006

(65) Prior Publication Data

US 2006/0149348 A1 Jul. 6, 2006

Related U.S. Application Data

(63) Continuation-in-part of application No. PCT/EP2004/013303, filed on Nov. 24, 2004.

(30) Foreign Application Priority Data

Nov. 27, 2003 (DE) .................................. 103 55 986

(51) Int. Cl.
*A61F 2/06* (2006.01)

(52) U.S. Cl. .......... 606/37; 623/1.1; 623/1.15; 606/157; 606/158

(58) Field of Classification Search .................... 623/1.1, 623/1.11, 1.15, 1.23, 1.39, 1.49, 1.24; 606/151, 606/157–158, 228; 128/898; 600/37
See application file for complete search history.

(56) References Cited

U.S. PATENT DOCUMENTS

| | | | | |
|---|---|---|---|---|
| 3,435,823 A * | 4/1969 | Edwards | .................. | 606/153 |
| 3,620,218 A * | 11/1971 | Schmitt et al. | ................ | 606/154 |
| 3,726,279 A * | 4/1973 | Barefoot et al. | ............... | 606/151 |
| 4,037,603 A * | 7/1977 | Wendorff | ....................... | 606/157 |
| D319,311 S * | 8/1991 | Kohler | ......................... | D24/143 |
| 5,147,389 A * | 9/1992 | Lane | ............................. | 623/1.24 |
| 5,211,649 A * | 5/1993 | Kohler et al. | .................. | 606/139 |
| 5,441,515 A * | 8/1995 | Khosravi et al. | .............. | 606/194 |
| 5,449,382 A * | 9/1995 | Dayton | ........................ | 623/1.15 |
| 5,476,471 A * | 12/1995 | Shifrin et al. | .................. | 606/151 |
| 5,527,355 A * | 6/1996 | Ahn | .............................. | 623/1.36 |
| 5,599,311 A * | 2/1997 | Raulerson | ..................... | 604/175 |
| 5,632,753 A * | 5/1997 | Loeser | .......................... | 606/151 |
| 5,702,343 A * | 12/1997 | Alferness | ........................ | 600/37 |
| 5,707,378 A * | 1/1998 | Ahn et al. | ..................... | 606/139 |
| 5,735,891 A * | 4/1998 | White | ............................ | 607/126 |
| 5,741,283 A * | 4/1998 | Fahy | ............................ | 606/157 |
| 5,824,038 A * | 10/1998 | Wall | .............................. | 623/1.12 |
| 5,876,419 A * | 3/1999 | Carpenter et al. | ............ | 623/1.16 |
| 5,957,975 A * | 9/1999 | Lafont et al. | ................. | 623/1.16 |
| 5,984,963 A * | 11/1999 | Ryan et al. | .................... | 623/1.11 |
| 6,071,306 A * | 6/2000 | Angelini | ....................... | 623/1.13 |
| 6,169,922 B1 * | 1/2001 | Alferness et al. | ................. | 607/5 |
| 6,193,648 B1 * | 2/2001 | Krueger | ......................... | 600/37 |
| 6,200,348 B1 * | 3/2001 | Biedermann et al. | ....... | 623/17.11 |
| 6,280,385 B1 * | 8/2001 | Melzer et al. | ................. | 600/423 |

(Continued)

FOREIGN PATENT DOCUMENTS

| | | |
|---|---|---|
| DE | 199 10 340 | 9/2000 |
| WO | 96/38090 | 12/1996 |

(Continued)

*Primary Examiner* — Corrine M McDermott
*Assistant Examiner* — Mark Mashack
(74) *Attorney, Agent, or Firm* — Klaus J. Bach

(57) ABSTRACT

In a compression sleeve for the local enclosure of a blood vessel or vein area comprising a retaining structure of a biocompatible material, the retaining structure is a flexible mat consisting of a mesh or net-like structure provided with an arrangement holding the retaining structure in a vein enclosing position.

7 Claims, 8 Drawing Sheets

U.S. PATENT DOCUMENTS

| | | | |
|---|---|---|---|
| 6,425,856 B1 * | 7/2002 | Shapland et al. | 600/37 |
| 6,520,983 B1 * | 2/2003 | Colgan et al. | 623/1.11 |
| 6,602,184 B2 * | 8/2003 | Lau et al. | 600/37 |
| 6,648,911 B1 * | 11/2003 | Sirhan et al. | 623/1.15 |
| 7,124,493 B2 * | 10/2006 | Lau et al. | 29/557 |
| 7,722,529 B2 * | 5/2010 | Yun | 600/37 |
| 7,981,103 B2 * | 7/2011 | O'Rourke et al. | 604/507 |
| 2002/0065449 A1 * | 5/2002 | Wardle | 600/37 |
| 2003/0139808 A1 * | 7/2003 | Shahinpoor et al. | 623/4.1 |
| 2004/0254632 A1 * | 12/2004 | Alt et al. | 623/1.15 |
| 2007/0004961 A1 * | 1/2007 | Case et al. | 600/37 |
| 2007/0265646 A1 * | 11/2007 | McCoy et al. | 606/157 |

FOREIGN PATENT DOCUMENTS

| | | |
|---|---|---|
| WO | WO 9638090 A1 * | 12/1996 |
| WO | WO 97/40755 | 11/1997 |
| WO | WO 9740755 A1 * | 11/1997 |
| WO | WO 2004/056274 | 7/2004 |
| WO | WO 2004056274 A1 * | 7/2004 |

* cited by examiner

COMPRESSION SLEEVE

This is a Continuation-In-Part Application of International Application PCT/EP2004/013303 filed Nov. 24, 2004 and claiming the priority of German application 103 55 986.8 filed Nov. 27, 2003.

BACKGROUND OF THE INVENTION

The invention relates to a compression sleeve for enshrouding a blood vessel or a vein valve area.

Weak tissues in a human body, in particular blood vessel tissue, will lead with increasing age to significant vessel expansions. This effect is particularly prominent when a body's valve systems in the blood circuit are expanded to such an extent that they do not work any more properly as unidirectional valves (check valves or flow control valves) so that backflow occurs at the valves and the blood vessels are exposed to additional internal pressures loads.

Without treatment, this effect results in the formation of varicose veins. Such veins are first formed by a widening of the blood vessels particularly in weak or resilient tissue areas or vessel walls. As a result, also the vein valves in the body for example in the area of the pelvis may expand and, in time, these valves generally fail. Finally, enhanced by the gravity, blood backup occurs resulting in further pressure exposure and further expansion of the veins, particularly in the legs. The dilation of the veins results first in varicose veins and finally in open legs.

These symptoms are treated by the use of support leggings which surround and compress the leg so that a counter pressure to the blood pressure is established and the blood vessel tissue stresses are relieved. However, the functionality of the vein valves of the body is not restored thereby.

For a lasting or preventative treatment of varicose veins however, it is important that the functionality of the veins and the vein valves is maintained or re-established. To avoid a dilation of veins or vein valves, it is necessary to reinforce the dilated vein tissue.

U.S. Pat. No. 5,500,014 discloses several embodiments of a support sleeve for blood vessels which are all tubular. As a result, for the installation of the sleeve, the blood vein has to be threaded through the vein that is, it first has to be cut. Furthermore, the support sleeves disclosed in this patent are not designed for growing rapidly together with the tissue of the veins.

It is therefore the object of the present invention to provide a compression sleeve which can be implanted without the need for cutting the vein and which is basically suitable for rapid growth into the vein tissue.

SUMMARY OF THE INVENTION

In a compression sleeve for the local enclosure of a blood vessel or vein area comprising a support structure of a bio-compatible material, the retaining structure is a flexible mat consisting of a mesh or net-like structure provided with a structure for holding the retaining structure in a vein enclosing position.

The mat forms a compression sleeve which may be for example of titanium or titanium nickel alloys and which is wrapped around the blood vessel particularly in the area where the tissue is weak or in the area of a vein valve.

It is important that the compression sleeve is formed from a flat mat. For the installation of the sleeve, it is therefore not necessary to first cut the vein like it is necessary for the installation of tubular sleeves but the mat is simply wrapped around the vein. For this reason, the compression sleeve also includes means which ensure that the mat remains wrapped around the vein, that is, that a mat once wrapped around a blood vein remains in place. Such means are preferably either hook structures, clamps, (separately provided or formed from the mat) or an elastic pretension of the mat or a combination of the means mentioned.

Generally, dilated blood vessels in any part of the body may lead to an aneurism that is to a locally limited blood vessel expansion which, if untreated will critically stress the tissue (pressure or stretching) so that the blood vessel may rupture and result in dangerous internal bleeding. As example, a stroke may be mentioned. Under such conditions also, the cutting of a vein for the installation of a sleeve around an endangered vein which is often in sensitive body areas (brain, heart, inner organs, arteries) is usually associated with high unpredictable risks and therefore unwarrantable. The present invention however permits the application of a sleeve around the vein by a minimally invasive procedure without the need for cutting the blood vessel even in body areas which are sensitive or difficult to access.

Another important features of the invention concerns the structure of the mat which must be so formed that it becomes ingrown into the blood vessel wall and, on the other hand, ensures deformability of the applied compression sleeve. For that reason, the mat is in the form of a mesh, a netlike structure, or an open porosity structure. With a net-like structure, the mat may consist of a metal sheet or a foil which is structured by known structuring processes such as laser cutting, etching or erosion methods.

It is also within the scope of the present invention to use a mat consisting of an electrically non-conductive material wherein the webs of the mat or of parts thereof have a metallic electrically conductive core. In this way, for example, certain electrical conductor configurations can be provided on the mat.

Preferably, the mat consists of a shape memory material for example a bio-compatible shape memory alloy (preferably nickel titanium alloy such as Nitanol®). With the respective material properties, two possible application variants can be realized. Both variants are equally suitable for an advantageous minimally invasive application of the compression sleeve.

In a first application variant, the predetermined superelasticity of the shape memory alloys is utilized. A mat preset in a rolled together state is elastically bent open for the installation around a blood vessel and surrounds the blood vessel simply by its elastic relaxation.

Alternatively, in a second application variant, a thermal shape memory effect of the shape memory alloy is utilized for the application of the compression sleeve. The shape memory alloy is selected under the consideration that, at a body temperature of 30 to 45° C., it has a predetermined shape (the mat is rolled up—state A) and keeps that shape, but below a switching temperature below the body temperature (minus 1 to 30° C.), a morphological conversion of the crystal grating causes a deformation of the material (straight-line mat, state B) Such a mat can be so designed that, in the state B, that is, at a temperature below 30° C., it can be placed adjacent a blood vessel so that, upon beating, the mat assumes its rolled-up shape and surrounds the blood vessel as it assumes the shape A.

The deformation and strength of the mat forming the compression sleeve can be designed individually after the determination of the needs for the particular blood vessel and the change-over to the shape of the undamaged, that is, unexpanded blood vessel. Among others, in the area of the jointure of the vena saphena magna with the vena femoralis, (area of the cross), a compression of the vena saphena magna is necessary as soon as its diameter becomes larger than 6 mm.

In the applied state, the compression sleeve assumes the function of an external stent, that is, of a support sleeve, which prevents a dilation of the respective vessel section. If the vessel is already dilated the external stent returns the blood vessel to the original state. In this state, the operation of a natural valve disposed in the area supported by the stent is re-established.

The invention will be described on the basis of actual embodiments below with reference to the accompanying drawings.

DETAILED DESCRIPTION OF PREFERRED EMBODIMENTS

Figure 1:
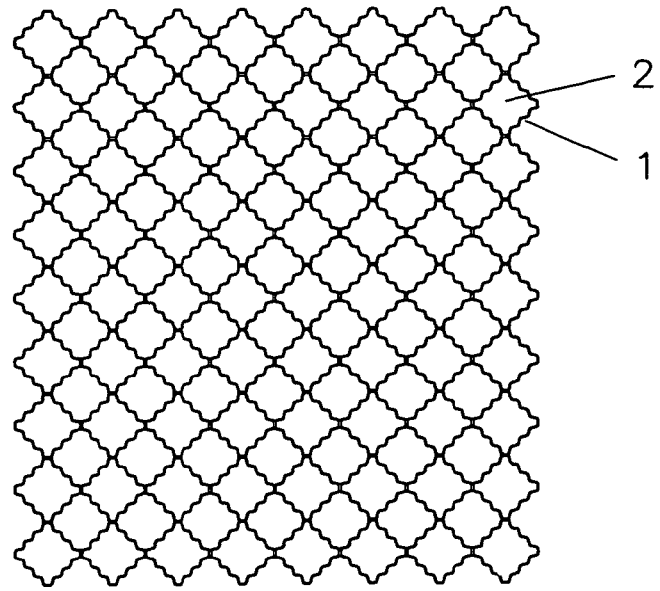
FIG. 1 shows a mat for a compression sleeve with a multitude of equally shaped cutouts disposed adjacent one another.
Figure 2A:
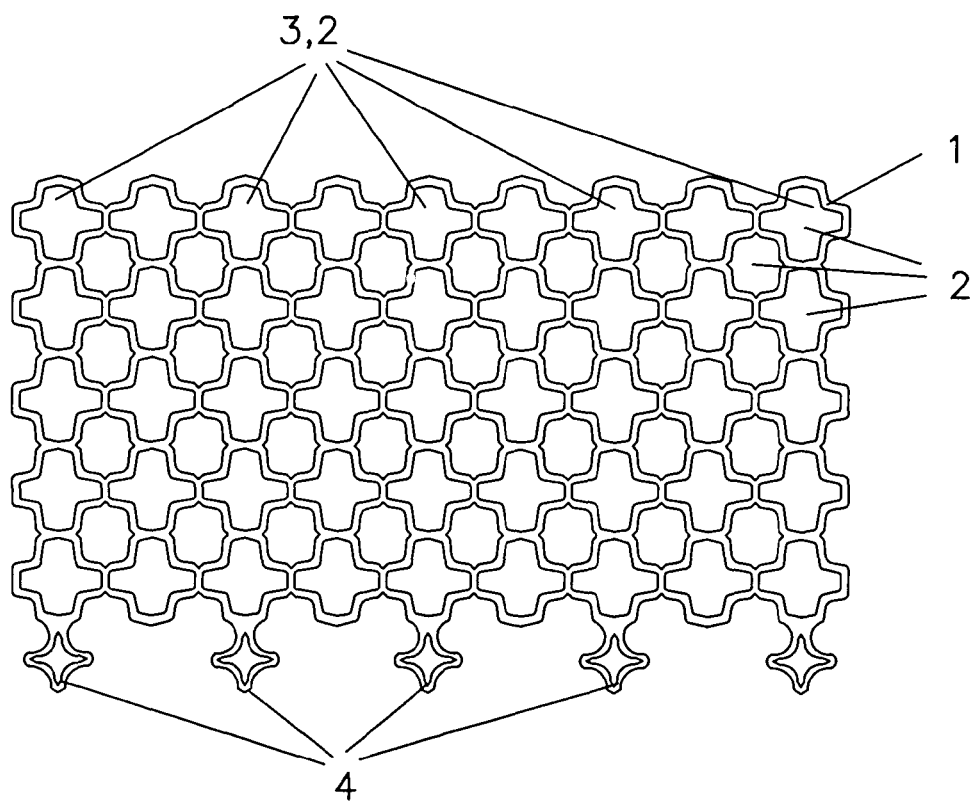
FIGS. 2a and 2b show each a compression sleeve with a multitude of equally shaped cut-outs of an alternate pattern and provided with hooks for the engagement of the opposite end of the mat upon installation around a blood vessel.
Figure 2B:
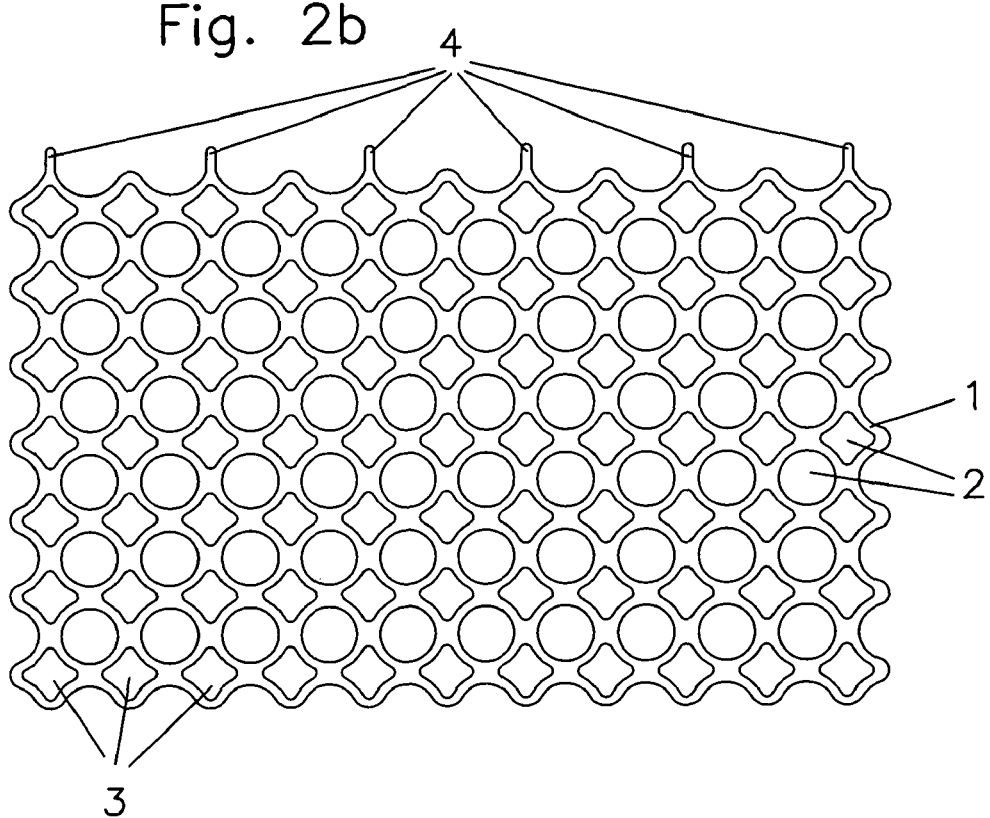

The FIGS. 1 to 3 show each a mat of a compression sleeve comprising webs 1 and openings 2. The FIGS. 2a and 2b as well as the FIGS. 3a to 3f show hooks 4, which, as shown in FIGS. 4a to 4c, are hooked into eyes 3 (corresponding to the web shape) in certain areas of the mat.

FIG. 1 shows a mat of a compression sleeve with a uniform, essentially square or rhombus-like, structure. Such a structure has a uniform elasticity in a diagonal direction of the squares of the structure but has a high rigidity parallel to the webs, that is, a high shape stability. For that reason, a compression sleeve structured in this way is suitable only for blood vessels which are not subjected to bending or expansions (not for example, for strongly pulsating main arteries). On the other hand, a relatively high shape stability is desirable for the stabilization of aneurisms. Hook structures are not shown in FIG. 1 (but are possible) so that a sleeve of this type maintains its shape exclusively by the elastic pretension in the mat. In this case, the mat can still be moved, that is reset, to a more desirable position before the in-growing of the mat into the tissue of the surrounded blood vessel. The mat consists of a bio-compatible material formed by laser cutting or stamping or of a metal foil or, alternatively, of a wire mesh.

FIGS. 2a and 2b show two embodiments wherein the mat comprises a plurality of adjacent geometric openings which alternate in shape. The webs are not oriented in one particular direction which provides for increased flexibility in the direction of the webs in comparison with the embodiment as shown in FIG. 1. The elastic expansion properties over the whole mat area however are about the same. As a result, such mats are suitable also for the encasing of blood vessels which are subjected to a limited bending and stretching. The mats include also hooks 4 which, after the mat is placed around a blood vessel, are inserted into openings which form retaining eyes. The hook mechanism type shown in FIG. 2a is shown in detail in FIG. 4c, that of FIG. 2b is shown in detail in FIG. 4a.

The FIGS. 3a to 3f show designs of mats for compression sleeves for particular applications. The embodiments shown in these figures differ basically by differently structured segments providing for locally different elastic expansion characteristics.

Figure 3A:
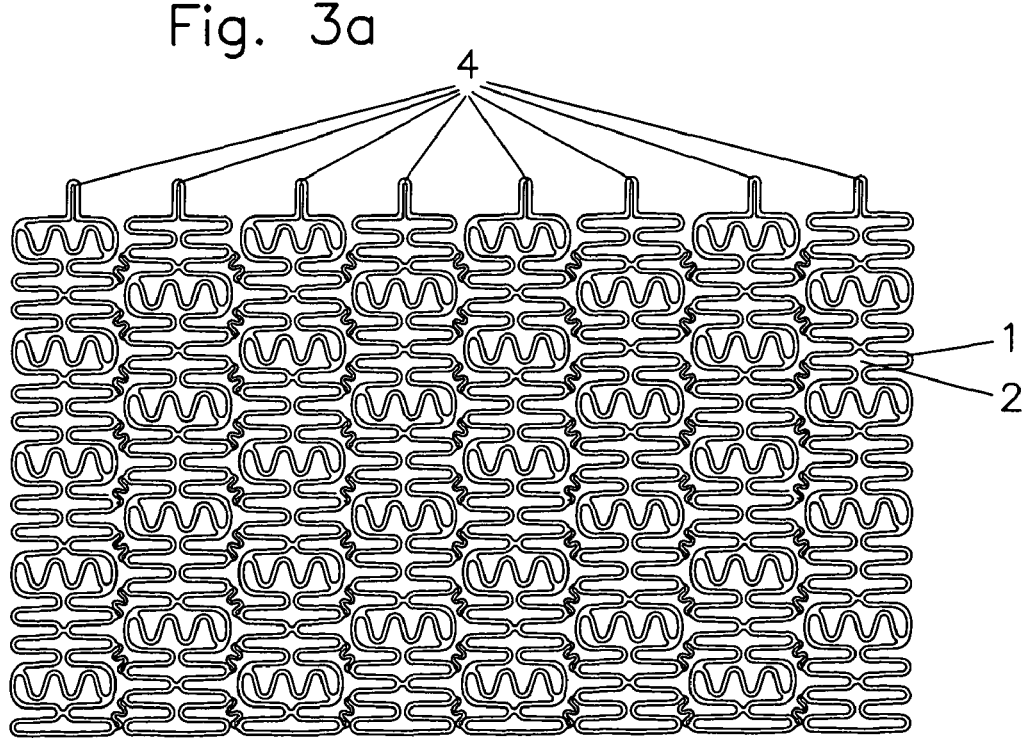
FIGS. 3a to 3f show various examples of compression sleeve mats having a meander shape.
Figure 4A:
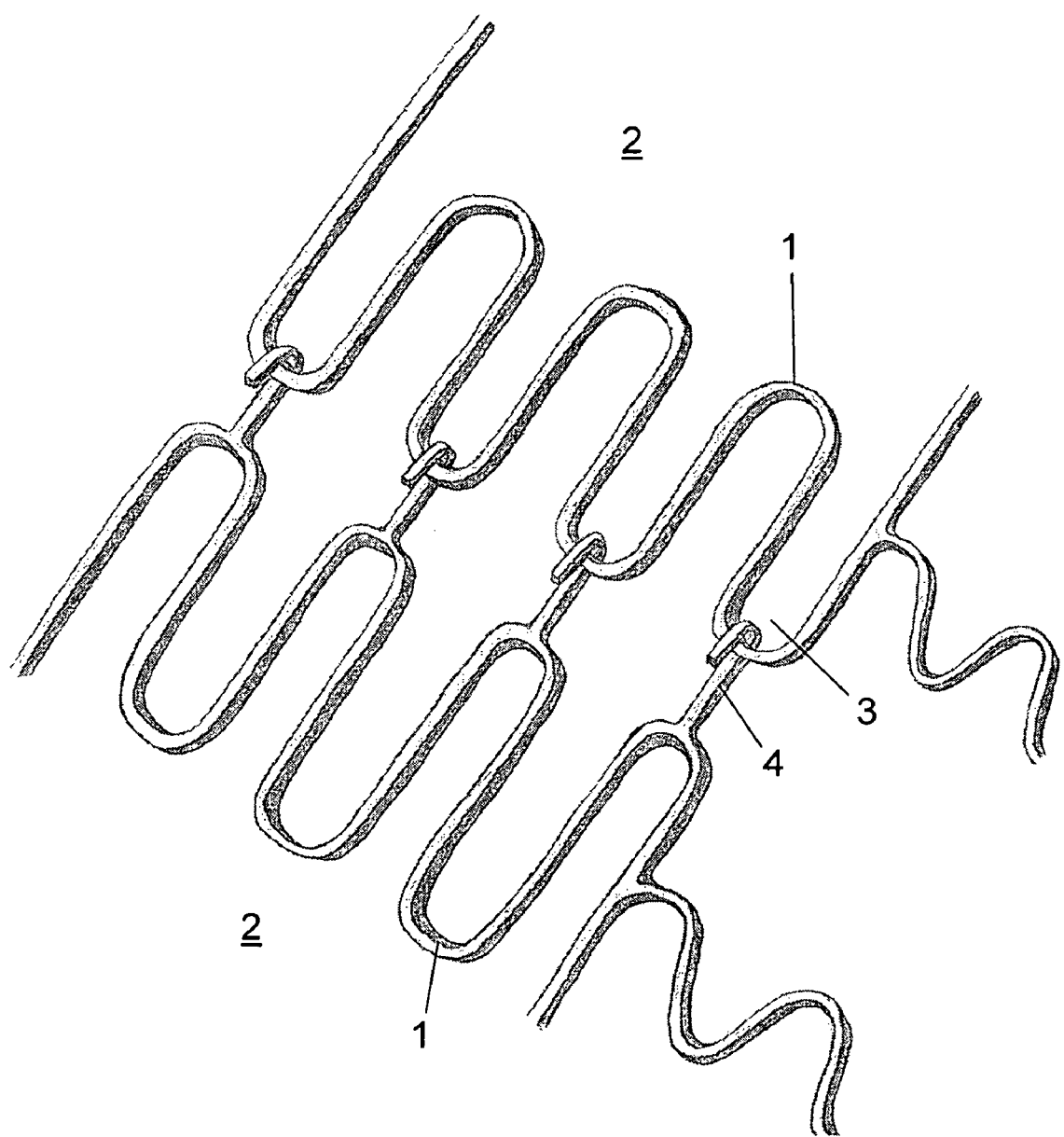
FIGS. 4a to 4c show three possible hook connections for the compression sleeve mats.
Figure 4B:
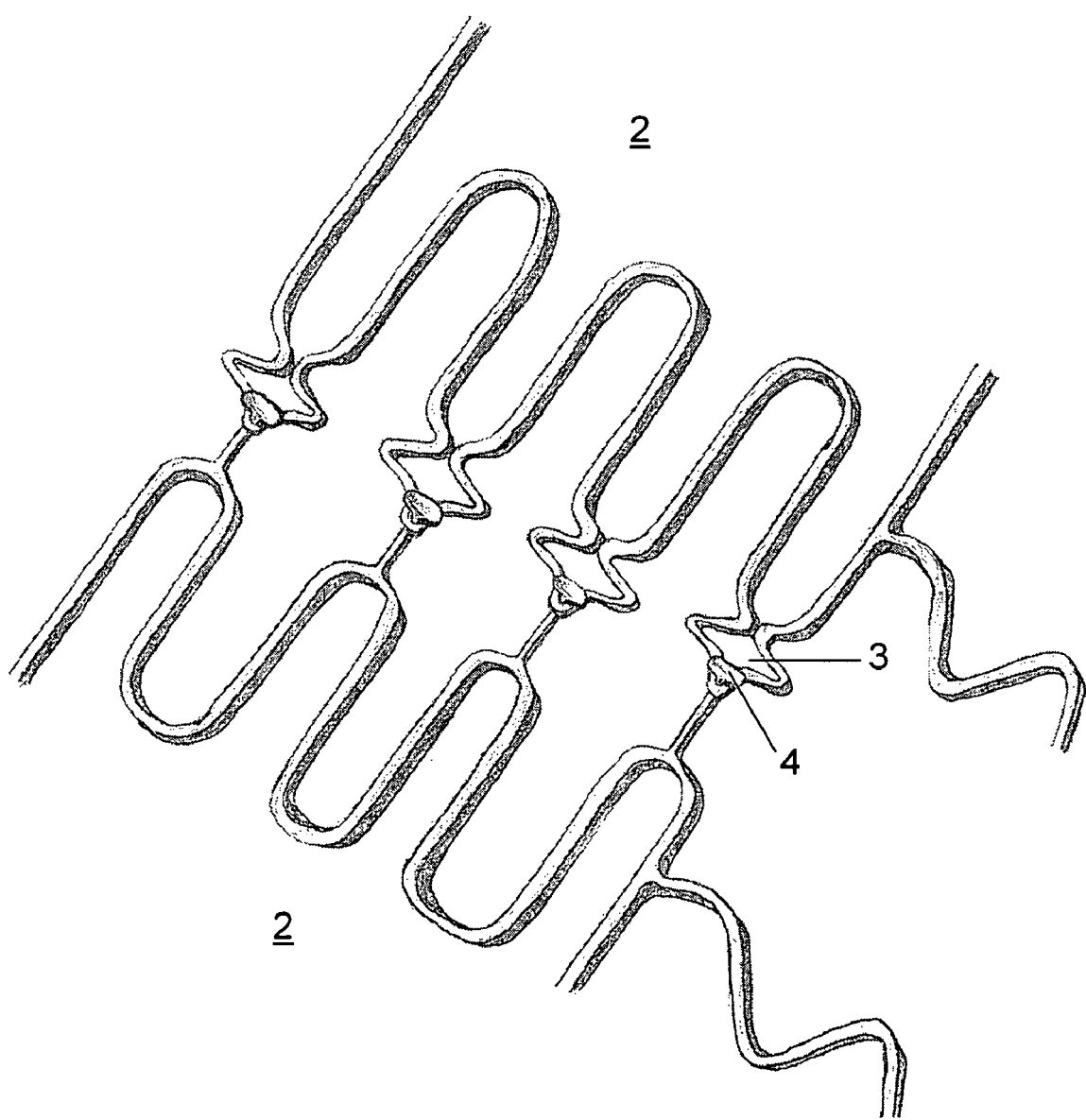
Figure 4C:
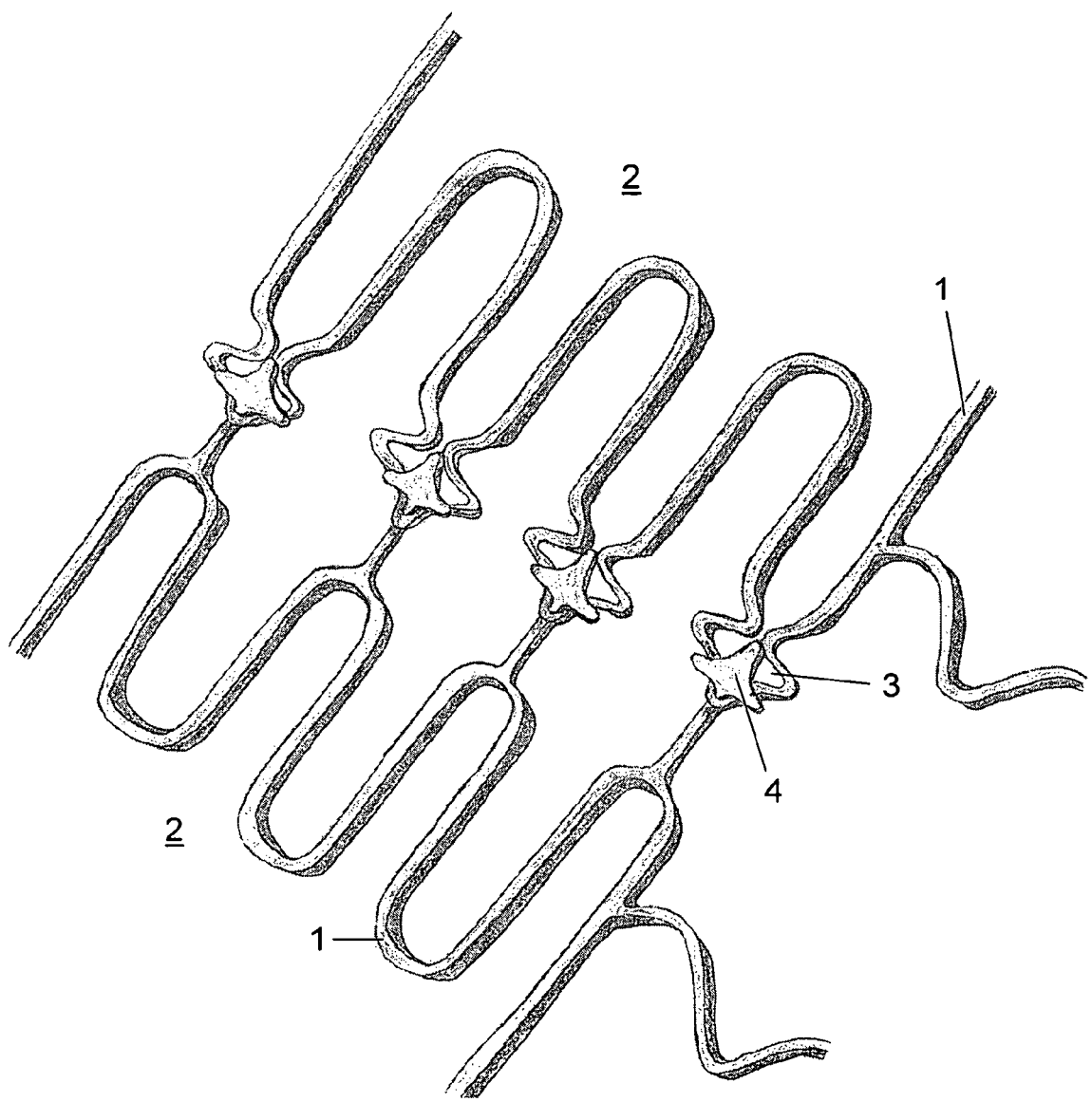

FIG. 3a shows a design with a particularly finely branched structuring wherein the webs are bent in large areas in a snakelike or meander-like manner and do not have a particular preferred orientation. This structure has a relatively large resiliency in all directions and the largely filigree-like structure causes a relatively fast in-growth of the sleeve into the blood vessel tissue. Such a compression sleeve structure is therefore particularly suitable for sleeving blood vessels which are frequently bent or expanded and for pulsating arteries or veins.

Figure 3B:
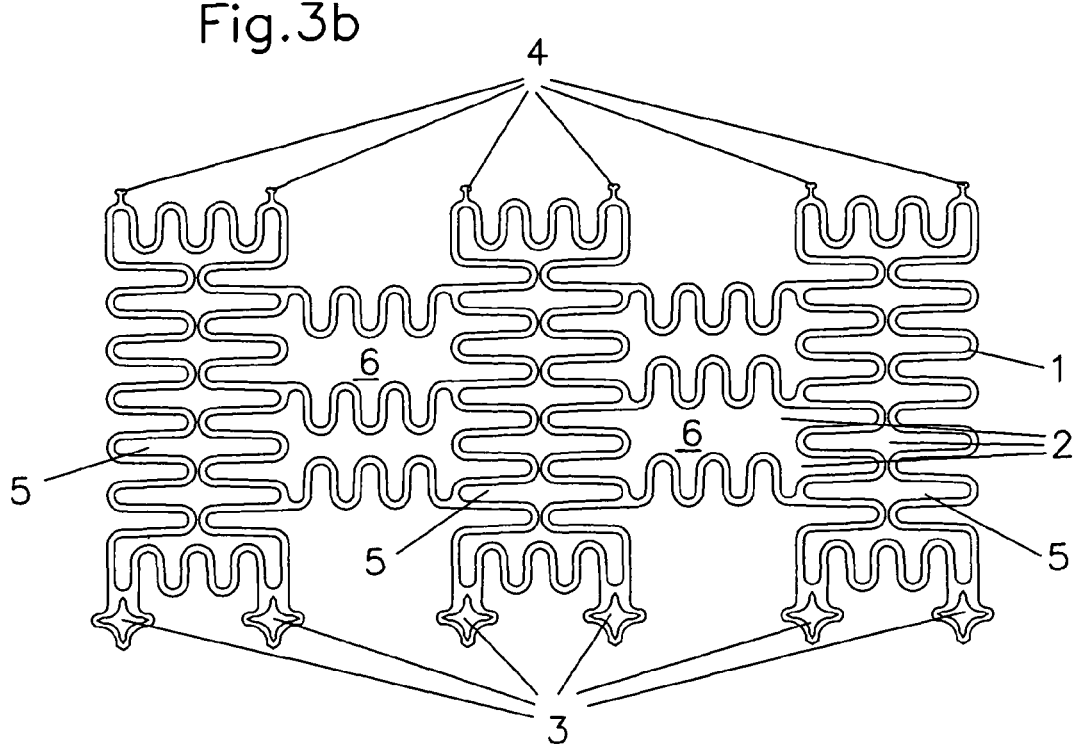
Figure 3C:
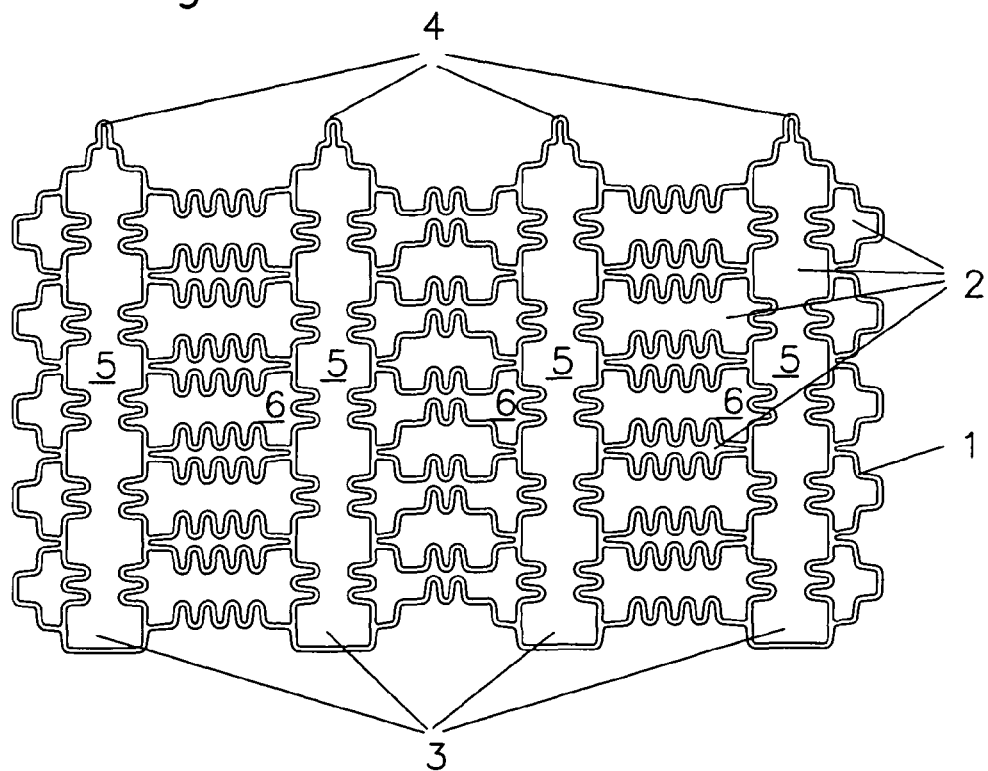

The embodiments of FIGS. 3b and 3c are based on similar design criteria wherein the structures however are less filigree-like and the openings between the webs are larger. The easily engageable and reliable hook mechanism 3 and 4 is shown in detail in FIG. 4b. FIGS. 3b and 3c show each a mat for a compression sleeve as it is preferred for temporary application around blood vessels, for example, for the stabilization of blood vessels during operations or healing processes.

FIG. 3b as well as FIGS. 3c to 3f represent mats for compression sleeves which comprise several areas. Each of the areas serves a particular purpose and therefore has a design structure as required for that purpose.

The embodiments as shown in FIGS. 3b to 3f comprise mats with two types of areas that is sleeving areas 5 and support areas 6. The sleeving areas serve the purpose of fixing the compression sleeve on the blood vessel and therefore also include the means required for that purpose that is the hook mechanism 3, 4. Between the sleeve areas are the support areas 6, which only support the blood vessel and do not contribute to the fixing of the compression sleeve to the blood vessel.

Figure 3D:
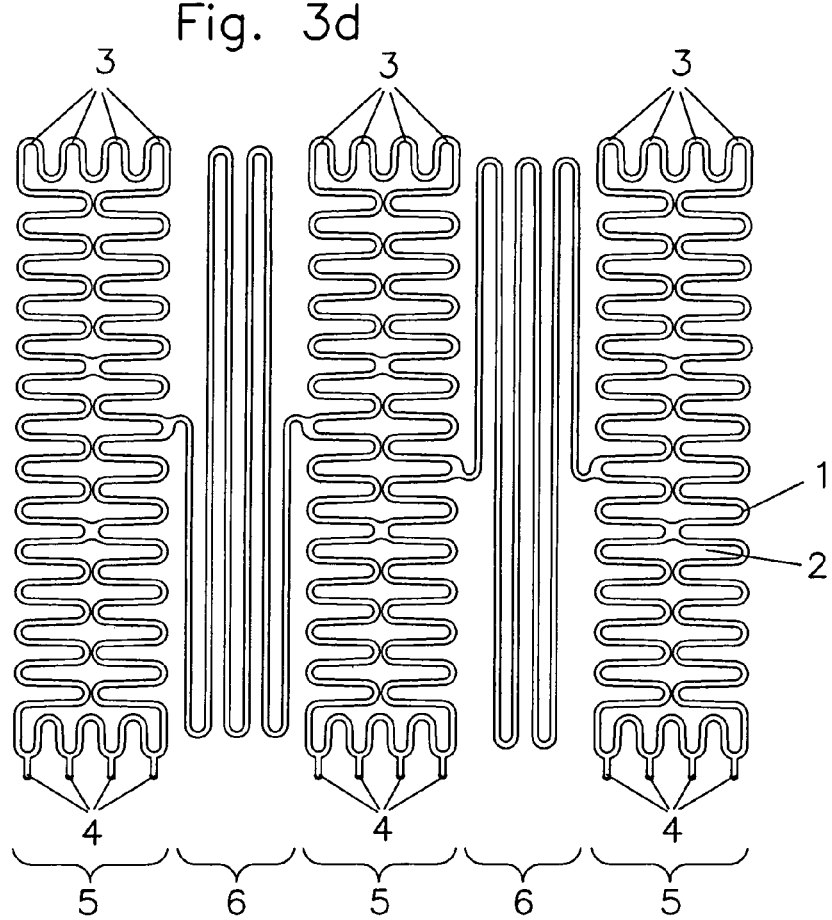

FIG. 3d shows an exemplary structure for a compression sleeve with a support area with a particularly high rigidity in radial direction and a particularly low axial rigidity. Blood vessel areas below the support area cannot expand radially and cannot contract. As a result, this embodiment is particularly suitable for supporting and stabilizing the vein's internal valves. The high radial resiliency interferes only slightly with the axial expansion of the blood vessels so that the blood vessel remains capable to compensate for a possible blood flow backup by axial expansion and possible complications can be obviated.

Figure 3E:
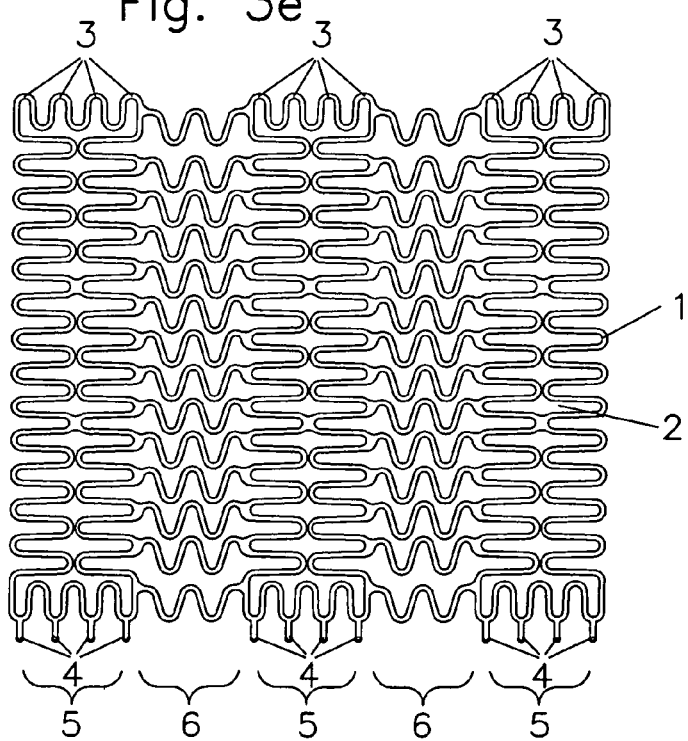
Figure 3F:
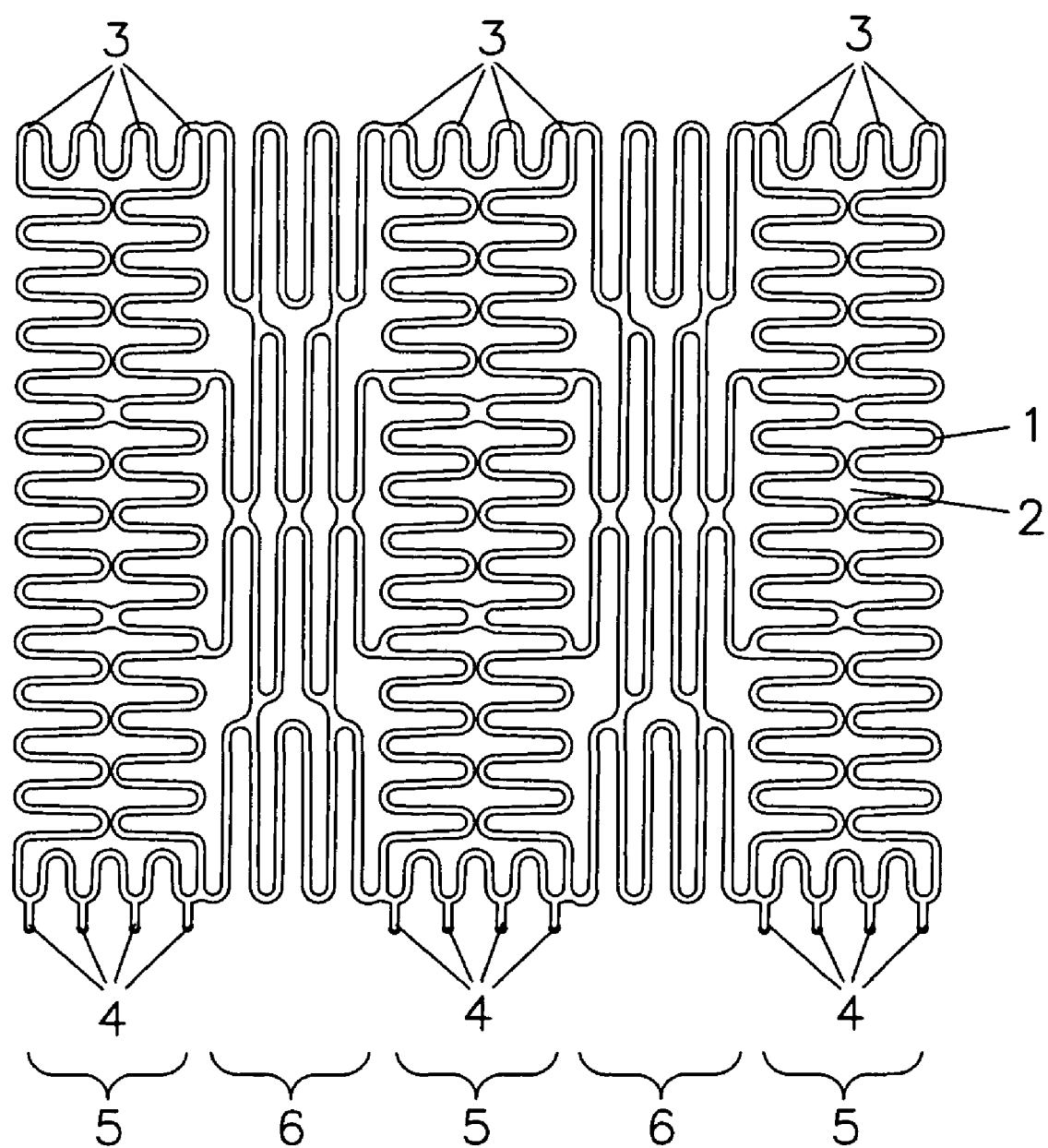

FIGS. 3e and 3g show structuring examples for a compression sleeve which, basically, is similar to that of FIG. 3d. However, the snake-like structured webs have in the sleeve areas 5, a substantially smaller amplitude which substantially reduces the axial resiliency in favor of a radial resiliency. Such embodiments are usable particularly for highly pulsating blood vessels.

FIGS. 4a to 4c show the hook structures 3, 4 referred to in connection with the description of earlier embodiments. As shown in the figures, they comprise correspondingly formed webs 1, wherein the hooks 4 are hooked into appropriately formed eyes 3, where they can be locked by appropriate bending. Depending on the application, the hooks can be hooked also into structure parts, other than the eyes, in the body of the mat. Again, as hooks also separate components or clips can be used with the same effect.

What is claimed is:

1. A compression sleeve for the local enclosure of a blood vessel or a vein valve area, comprising a flexible mat of a bio-compatible material for wrapping around the blood vessel and means for maintaining the mat wrapped around the blood vessel, said mat consisting of a foil with a plurality of openings cut out of the foil by one of a laser cutting, etching, and erosion method so as to form a flat, thin mesh, or net-like structure with flat thin webs extending around the openings.

2. A compression sleeve according to claim 1, wherein the biocompatible material comprises a shape memory material.

3. A compression sleeve according to claim 2, wherein the biocompatible material is a nickel titanium alloy and the structured mat is formed from one of a sheet cut by laser cutting and a wire mesh.

4. A compression sleeve according to claim 3, wherein the mat includes a plurality of rhombus-shaped openings disposed adjacent one another over the whole area of the mat.

5. A compression sleeve according to claim 1, wherein the means for maintaining the mat wrapped around the blood vessel are hook-like structures.

6. A compression sleeve according to claim 1, wherein the means for mounting the mat comprises a memory shape material which, at body temperature, holds the mat in a curled shape.

7. A compression sleeve according to claim 1, wherein the structured mat forms an inductor which is part of an electromagnetic oscillation circuit.

* * * * *